Sept. 10, 1940. J. D. BROWNELL Plant Pat. 419
ROSE PLANT
Filed Sept. 6, 1939
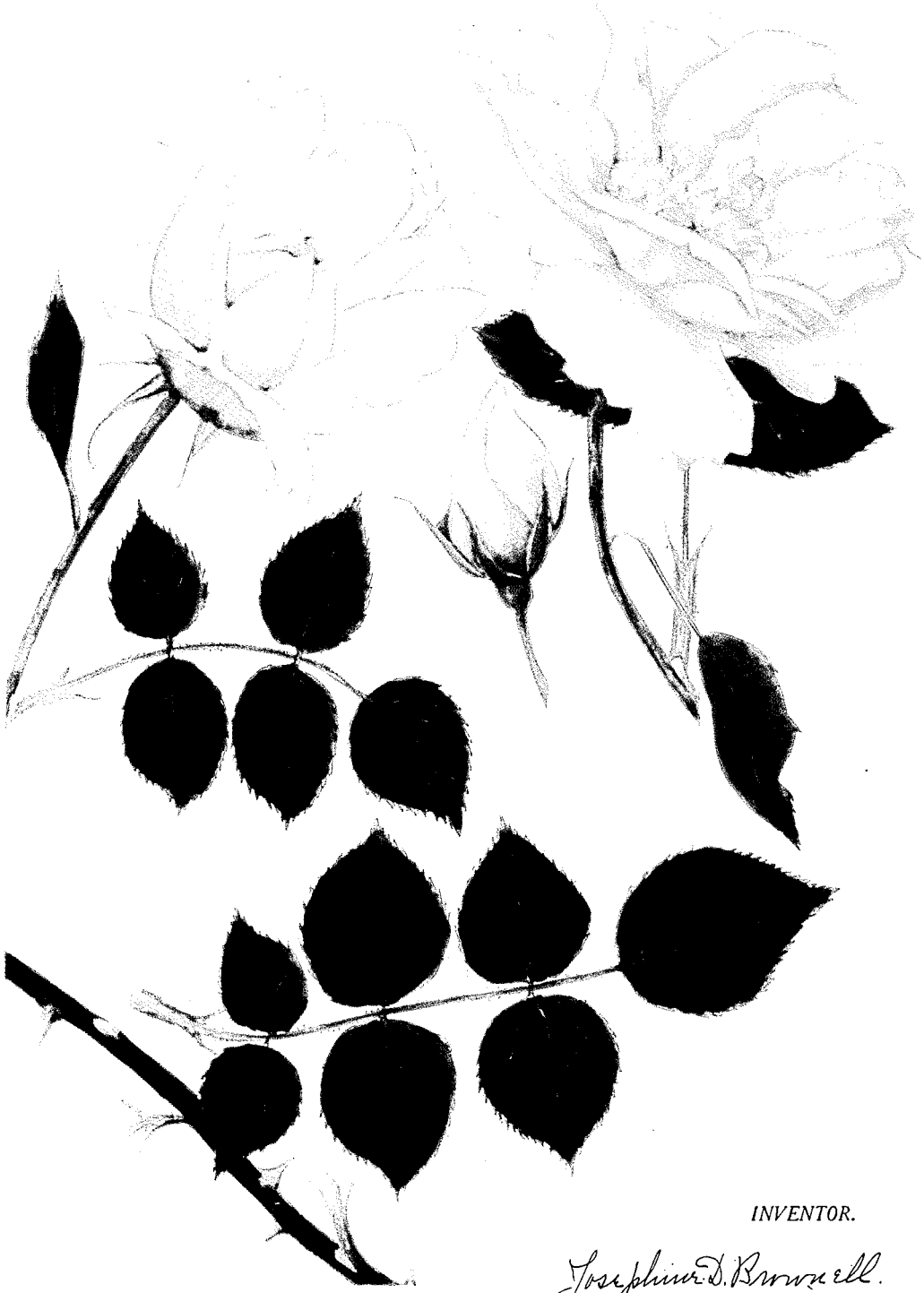
INVENTOR.
Josephine D. Brownell.

Patented Sept. 10, 1940

Plant Pat. 419

UNITED STATES PATENT OFFICE

419

ROSE PLANT

Josephine D. Brownell, Little Compton, R. I.

Application September 6, 1939, Serial No. 293,557

1 Claim. (Cl. 47—61)

My invention relates to roses and especially to a new and original and distinct variety, of the class known commercially as hardy climbing roses and to a subdivision of that class which by virtue of a creeping or trailing habit adapts itself also for use as ground, wall and fence cover and embankment decoration, which might be designated as trailing or creeping; also with the habit of growing vigorously held in an upright position over trellis, arbor or other support; produced by me and under my directions in the breeding grounds of my research gardens at Little Compton, Rhode Island, by propagation and by cross pollination, which can be and has been asexually reproduced.

My new rose is new as to the following characteristics and especially as to their joint association in connection with the characteristics of hardiness or immunity from serious injury on account of cold temperatures prevailing in certain parts of the northern portion of the United States;

The unique red and yellow nearly self-toned color effect of the petals;

The semidouble character and variation within certain definite limits of the form of the bloom;

Its character of fragrance;

Its climbing or trailing habit in combination with its branching habit.

In the accompanying drawing forming a part of this specification I have shown my new rose in its natural colors, that is as near as is possible to do so artificially.

I otherwise describe my new rose as follows:

My new rose plant is a hardy hybrid climbing or trailing *Rosa wichuraiana,* crossed in its ancestral generations with, in addition to *Rosa wichuraiana* several so called hybrid tea and species roses.

My new rose plant is otherwise described as follows.

Essential Information

*Type*

Hardy climbing to nearly decumbent; outdoor; seedling; for cut flowers, garden decoration, dooryard and roadside display.

*Class*

Hybrid climbing *wichuraiana;* subdivision climbing trailer.

*Breeding or discovery*

The pollination which produced my new rose was directed by me and made July 6, 1930*, in my research garden; this seed was planted December 20, 1930, in the greenhouse in Little Compton, Rhode Island, and there germinated in February 1931. The plant therefrom was planted in my said garden in May 1931. This plant can be and has been by me and under my direction asexually reproduced by budding in my said gardens during the months of July and August in the years 1932 to 1936 inclusive; the characters of the original seedling were thereby reproduced.

The genealogy of my new rose is to the best of my knowledge and belief as follows: it is a hybrid descendant, the pollen parent being the same as the pollen parent of the climbing rose commercially known as Golden Glow and the seed parent being the same as the seed parent of the climbing rose commercially known as Apricot Glow (Plant Patent No. 200).

The cross which produced my new rose was made by me under my directions as follows: a flower of the seed parent was emasculated before the opening of any of its anthers, it was promptly covered with a wax paper bag firmly secured at the base as protection against self and foreign pollen. When the stigmas were receptive the bag was momentarily removed and the pollen applied with a camel's hair brush and the bag replaced. The hip was picked in November of the same year.

*Propagation*

It has held its distinguishing characteristics through succeeding propagations by budding.

Flower

*Habit*

It blooms outdoors in Little Compton, Rhode Island, in late June and July and begins to bloom about five days before the climbing rose Dr. W. van Fleet begins to bloom.

*Flowers borne*

Usually one to five and when well established frequently more on each stem; in regular hybrid tea type of clusters, usually on strong, woody stiff stems, slender and frequently arching bearing small clusters and large stems usually upright bearing larger clusters.

*Quantity of bloom*

Abundant outdoors in full sunshine, especially on canes and branches in arching to horizontal position.

*Continuity*

One season of three to five weeks according to age and size of plants.

* This and other dates herein are approximate.

*Fragrance*

Mild pleasing, China Tea in combination with *Rosa wichuraiana.*

*Bud*

Size, medium, pointed to slightly ovoid, opens well, being not at all affected by wet or hot weather at Little Compton, Rhode Island.

Peduncle, medium in length, thickness medium to light, erect to stiff, color* Calliste Green shading to Purplish Vinaceous, with slight variations therefrom variable on different stems.

Foliaceous appendages are notably rare.

Color: as calyx breaks and bud begins to open, outer side of petals at top Spectrum Red to Carmine shading downward slightly deeper toward Oxblood Red.

*Bloom*

Is usually 4 to 5 inches when fully open and occasionally larger, semi-double with slightly variable number of petals, usually averaging about 15 with one to five petaloids. The flower opens high centered and the petals somewhat recurled, form similar to the popular hybrid tea type of bloom, clearly showing when open many of the pistils and stamens.

Petals are in form somewhat variable, outer petals being broadly obovate, inner petals usually narrower, edges frequently variably irregular throughout, being often scalloped to indented to irregularly notched. Texture thick, substantial and leathery, both surfaces satiny to shiny.

Color of opening flower, outer petals outside top Begonia Rose to slightly more violet shading downward to Spectrum Red to slightly more violet. Inner side Begonia Rose to slightly more violet on upper border shading downward to Strawberry Pink at center to Light Salmon Orange to lighter toward Orange Pink at base. The tone color between opening petals is Spectrum Red to slightly more violet.

The flower has a mild and delicate tea rose fragrance in combination with the fragrance of *Rosa wichuraiana.*

The petals usually drop off cleanly.

*Reproductive organs*

The stamens are slightly variable, medium in quantity, slightly uneven in length, the anthers are Capucine Yellow.

Filaments medium in length and color near base is Bittersweet Orange.

Styles are splashed with Spectrum Red and stigmas Pale Orange Yellow.

The ovaries do not protrude from the calyx lobe.

PLANT

*Foliage*

Abundant, of compound leaflets, frequently of one or three leaflets on stem near the flower and five on lower leaves and usually seven leaflets on the canes and occasionally near base of the larger flower stems.

The leaflets are nearly round to oval with prominent, moderately acute apexes with slightly variable rounded bases. The terminal leaflet is usually slightly larger and the two at the base of the seven leafleted leaves are usually notably smaller.

Distinctive characteristics of the leaflets are thickness and rigidity at maturity, the dark color and glassy surface of the upper side, late seasonal persistence, combining to suggest holly like foliage.

The color of the upper surface at full maturity is Civette Green on the three leafleted leaves, to Rinnemann's Green on larger leaves, under side Asphodel Green, edges of mature leaflets overlaid with Rose Red, as is the younger growth.

The rachises are medium slender much the same color of the leaflets and similarly overlaid, with minute hairs on the upper edges of the outer sides, and few small prickles on the under side, hooked downward and before late maturity are shaded from the overlay color toward Spectrum Red, turning lighter at full maturity.

The stipules are variable in length frequently notably long and narrow, to an inch and one-half in length and about one-quarter inch wide, with thin points which normally spread about 80 degrees in relation to each other. The edges have minute hairs.

New canes and branches are medium in size and the color is Calliste Green shading frequently on one side to Kronberg's Green.

Prickles on canes, branches and stems are medium to few, nearly straight, medium to small and in color shade from the color of the bark on which they grow to the color of the overlay variable to nearly Spectrum Red, later turning lighter to dull wood color.

The plant is unusually resistant to black spot and mildew, and requires no dusting or spraying at Little Compton, Rhode Island, under normal conditions.

*Growth*

Habit is repent or creeping, as a trailing vine upon the ground, the canes normally lying in a recumbent to decumbent position, substantially in the manner of its ancestor *Rosa wichuraiana,* due to the trait of the angle of equilibrium of the canes being nearly 90 degrees in relation to the gravitational influence. Canes and branch growth usually starts from side eyes but an eye on the upper surface of a branch or cane will occasionally start to grow usually developing to arch downward and assume the normal growth angle. Neighboring environmental conditions may hold branch growth in abnormal upright position in which the wood will harden. Consequently the habit of growth is not normally quite as prostrate as is that of the species ancestor *Rosa wichuraiana,* but is sufficiently so that it may be appropriately grown as a ground cover or embankment decoration. About 95% of the cane growth will lie normally recumbent upon the ground and about 5% will lie slightly above averaging about six inches high; or it will grow tied in the usual positions for growing climbing or pillar roses, blooming freely in all such positions. The new canes in recumbent position may grow fifteen to twenty feet or more in one season, in vertical position they grow much less, laterals therefrom developing vigorously and the vertical growth developing thickness of hard woody growth with abnormal rapidity.

*Winter resistance*

From tests at Little Compton, Rhode Island, my new rose plant compares in winter resistance about the same as that of Dr. W. van Fleet.

*Comparisons*

I know of no rose plant that compares closely with my new rose plant. In comparison with those frequently grown featuring their trailing habit, *Rosa wichuraiana* has leaflets very much

* Color references unless otherwise stated are to Ridgway.

smaller, the flowers are very much smaller, their color is white with yellow stamens. Max Graff, the foliage is suggestive of *Rosa rugosa* the flower is very much lighter and much nearer violet. To Rugosa Repens Alba the last foliage differentiation applies and the color is nearly white. The flower of my new rose plant is of hybrid tea character and probably resembles as much as any hybrid tea flower that of Carillon.

I claim:

The hardy hybrid *Rosa wichuraiana* large flowered climbing and repent rose plant with hybrid tea type of flower and bloom cluster, characterized by its resistance to winter injury, its mild pleasing fragrance, with notably holly like foliage with form and color substantially as shown, being nearly spectrum red outside of petals and lighter and of more yellow tones within.

JOSEPHINE D. BROWNELL.